(12) United States Patent
Kitagawa et al.

(10) Patent No.: US 11,499,093 B2
(45) Date of Patent: Nov. 15, 2022

(54) RARE EARTH COMPLEX AND LIGHT EMITTING ELEMENT

(71) Applicant: NATIONAL UNIVERSITY CORPORATION HOKKAIDO UNIVERSITY, Sapporo (JP)

(72) Inventors: Yuichi Kitagawa, Sapporo (JP); Fumiya Suzue, Sapporo (JP); Takayuki Nakanishi, Sapporo (JP); Koji Fushimi, Sapporo (JP); Yasuchika Hasegawa, Sapporo (JP)

(73) Assignee: NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 586 days.

(21) Appl. No.: 16/488,784

(22) PCT Filed: Feb. 22, 2018

(86) PCT No.: PCT/JP2018/006466
§ 371 (c)(1),
(2) Date: Aug. 26, 2019

(87) PCT Pub. No.: WO2018/155557
PCT Pub. Date: Aug. 30, 2018

(65) Prior Publication Data
US 2020/0063030 A1 Feb. 27, 2020

(30) Foreign Application Priority Data
Feb. 27, 2017 (JP) .............................. JP2017-035043

(51) Int. Cl.
| | | |
|---|---|---|
| *C09K 11/06* | (2006.01) | |
| *C07C 49/163* | (2006.01) | |
| *C07C 49/323* | (2006.01) | |
| *C07F 9/53* | (2006.01) | |
| *H01L 33/50* | (2010.01) | |

(52) U.S. Cl.
CPC ............ *C09K 11/06* (2013.01); *C07C 49/163* (2013.01); *C07C 49/323* (2013.01); *C07F 9/53* (2013.01); *H01L 33/501* (2013.01); *C09K 2211/1011* (2013.01)

(58) Field of Classification Search
None
See application file for complete search history.

(56) References Cited

U.S. PATENT DOCUMENTS

| | | | | |
|---|---|---|---|---|
| 5,435,937 | A | * 7/1995 | Bell ................. | C09K 11/04 556/26 |
| 6,524,727 | B1 | * 2/2003 | Kathirgamanathan ...................... | H05B 33/14 313/506 |
| 7,242,443 | B2 | * 7/2007 | Sage .................. | C09K 11/06 252/301.16 |
| 2008/0171858 | A1 | * 7/2008 | Nagata ............... | H05B 33/14 534/15 |
| 2010/0072424 | A1 | 3/2010 | Petoud et al. | |
| 2016/0160121 | A1 | 6/2016 | Hasegawa et al. | |
| 2016/0164012 | A1 | 6/2016 | Lee et al. | |

FOREIGN PATENT DOCUMENTS

| | | | |
|---|---|---|---|
| CN | 103320117 A | * 12/2012 | ............. C07F 19/00 |
| CN | 102807592 A | * 9/2013 | ............. C09K 11/06 |
| JP | 2007269780 A | * 10/2007 | ............... C07F 9/30 |
| JP | 2010-77058 A | 4/2010 | |
| JP | 2010-278376 A | 12/2010 | |
| JP | 2016-128392 A | 7/2016 | |
| JP | 2016-166139 A | 9/2016 | |
| KR | 10-2016-0043553 A | 4/2016 | |

(Continued)

OTHER PUBLICATIONS

Kitagawa et al. "Visible luminescent lanthanide ions and a large π-conjugated ligand system shake hands." Physical Chemistry Chemical Physics 18, No. 45 (2016): 31012-31016. (Year: 2016).*

(Continued)

*Primary Examiner* — Robert S Loewe
(74) *Attorney, Agent, or Firm* — Sughrue Mion, PLLC

(57) ABSTRACT

A rare earth complex including a rare earth ion and a ligand coordinated with the rare earth ion and having a condensed polycyclic aromatic group. The condensed polycyclic aromatic group is a residue formed by removing a hydrogen atom from a condensed polycyclic aromatic compound represented by the following formula (I) or (II):

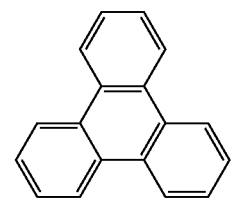

(I)

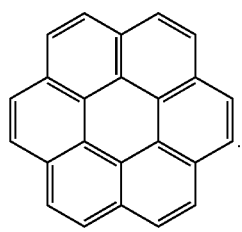

(II)

5 Claims, 6 Drawing Sheets

(56) References Cited

FOREIGN PATENT DOCUMENTS

| KR | 10-2016-0069021 A | 6/2016 |
|---|---|---|
| WO | 2010032395 A1 | 3/2010 |
| WO | 2015002295 A1 | 1/2015 |
| WO | 2015/115532 A1 | 8/2015 |

OTHER PUBLICATIONS

Osawa et al. "Intra-complex energy transfer of europium (III) complexes containing anthracene and phenanthrene moieties." The Journal of Physical Chemistry A 113, No. 41 (2009): 10895-10902. (Year: 2009).*

STN International, Database Registry, Jun. 2, 2021 (2021), RN 1491172-53-2, RN 1491172-50-9, RN1491172-47-4, RN 1491172-44-1, RN 1491172-41-8, pp. 1-5 (5 pages total).

"Database Registry, RN 1491172-53-2, RN 1491172-50-9, RN1491172-47-4, RN 1491172-44-1, RN 1491172-41-8", STN international [online], 2013, pp. 1-3.

Pietraszkiewicz, O. et al., "Highly photoluminescent Eu(III) complexes of the new 1-triphenylen-2-yl-3-trifluoroacetylacetone", Journal of Photochemistry and Photobiology, A: Chemistry, 2012, vol. 250, pp. 85-91.

Baek, N. S. et al., "Sensitized near IR luminescence of Er(III) ion in lanthanide complexes based on diketone derivatives: synthesis and photophysical behaviors", Bulletin of the Korean Chemical Society, 2007, vol. 28, No. 8, pp. 1256-1260.

Gong, Y. et al., "A highly stable dynamic fluorescent metal-organic framework for selective sensing of nitroaromatic explosives", Chemical Communications, 2013, vol. 49, pp. 11113-11115 (16 pages total).

Klink, S. I. et al., "A Systematic Study of the Photophysical Processes in Polydentate Triphenylene-Functionalized $Eu^{3+}$, $Tb^{3+}$, $Nd^{3+}$, $Yb^{3+}$, and $Er^{3+}$ complexes", Journal of Physical Chemistry A, 2000, vol. 104, pp. 5457-5468.

Klink, S. I, et al., "Sensitized near-infrared luminescence from polydentate triphenylene-functionalized $Nd^{3+}$, $Yb^{3+}$, and $Er^{3+}$ complexes", Journal of Applied Physics, 1999, vol. 86, No. 3, pp. 1181-1185 (6 pages total).

Steemers, F. J. et al., "New Sensitizer-Modified Calix[4]arenes Enabling Near-UV Excitation of Complexed Luminescent Lanthanide Ions", Journal of the American Chemical Society, 1995, vol. 117, pp. 9408-9414.

Pozniak, B. P. et al., "Monomer and Dimer Complexes of Coronene with Atomic Ions", J. Am. Chem. Soc., 1997, vol. 119, pp. 10439-10445.

Gong, Y. et al., "Photochromism, photoluminescence modulation and selective recognition of small molecules of two highly stable dynamic metal-organic frameworks", Dalton Transactions, Oct. 2017, vol. 46, pp. 15656-15660.

Naotaka Yamamoto et al., "Synthesis and Immobilization of Vapochromic luminescent Platinum(II) Complex to Nanoparticle", The 67th Conference of the Japan Society of Coordination Chemistry, Sep. 1, 2017, p. 356.

Fumiya Suzue et al., "Syntheses and Luminescence Properties of Europium(III) Complexes Containing Triphenylene Frameworks", The 97th CSJ Annual Meeting, Mar. 3, 2017, pp. 1-3.

International Search Report dated May 29, 2018 from the International Searching Authority in counterpart International Application No. PCT/JP2018/006466.

International Preliminary Report on Patentability dated Aug. 29, 2019 from the International Bureau in counterpart International Application No. PCT/JP2018/06466.

* cited by examiner

RARE EARTH COMPLEX AND LIGHT EMITTING ELEMENT

CROSS REFERENCE TO RELATED APPLICATIONS

This application is a National Stage of International Application No. PCT/JP2018/006466, filed on Feb. 22, 2018, which claims priority from Japanese Patent Application No. 2017-035043, filed on Feb. 27, 2017.

TECHNICAL FIELD

The present invention relates to a rare earth complex and a light emitting element.

BACKGROUND ART

A rare earth complex which exhibits emission of red light is expected to be applied to, for example, as fluorescent substance to constitute a white LED light source. As the rare earth complex which exhibits emission of red light, for example, a europium complex having a hexafluoroacetylacetonate (hfa) derivative and a phosphine oxide compound as ligands has been reported (Patent Literature 1).

CITATION LIST

Patent Literature

Patent Literature 1: Japanese Unexamined Patent Publication No. 2016-166139

SUMMARY OF INVENTION

Technical Problem

The excitation wavelength band (absorption wavelength) of an intensive light-emitting rare earth light-emitting substance is typically at 400 nm or less. On the other hand, the general-purpose excitation wavelength of light-emitting substance of a white LED light source is in the vicinity of 460 nm in the visible light region excited by a blue LED. When it becomes possible that a rare earth light-emitting substance is excited by a blue LED, creation of a new market is expected due to an advantage of excellent color rendering.

A main object of the present invention is to provide a novel rare earth complex which efficiently emits light by excitation using visible light in the vicinity of 460 nm.

Solution to Problem

In an aspect of the present invention, there is provided a rare earth complex comprising a rare earth ion and a ligand coordinated with the rare earth ion and having a condensed polycyclic aromatic group. The condensed polycyclic aromatic group is a residue formed by removing a hydrogen atom bonded to a condensed aromatic ring in the following formula (I) or formula (II) from a condensed polycyclic aromatic compound represented by formula (I) or (II). The condensed polycyclic aromatic compound optionally has a substituent bonded to the condensed aromatic ring in formula (I) or formula (II).

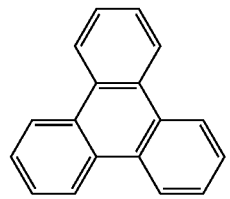
(I)

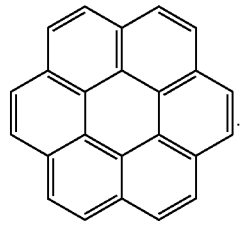
(II)

The present invention also relates to a light emitting element comprising the rare earth complex described above. The light emitting element is usable as various light sources such as a white LED and an optical coherence tomography apparatus.

Advantageous Effects of Invention

According to the present invention, there is provided a novel rare earth complex which efficiently emits light by excitation using visible light (for example, 420 to 480 nm). Further, the rare earth complex in an embodiment of the present invention tends to exhibit emission in a relatively narrow emission band in the emission spectrum, so that application to a light emitting element is advantageous from this point of view.

DESCRIPTION OF EMBODIMENTS

Figure 1:
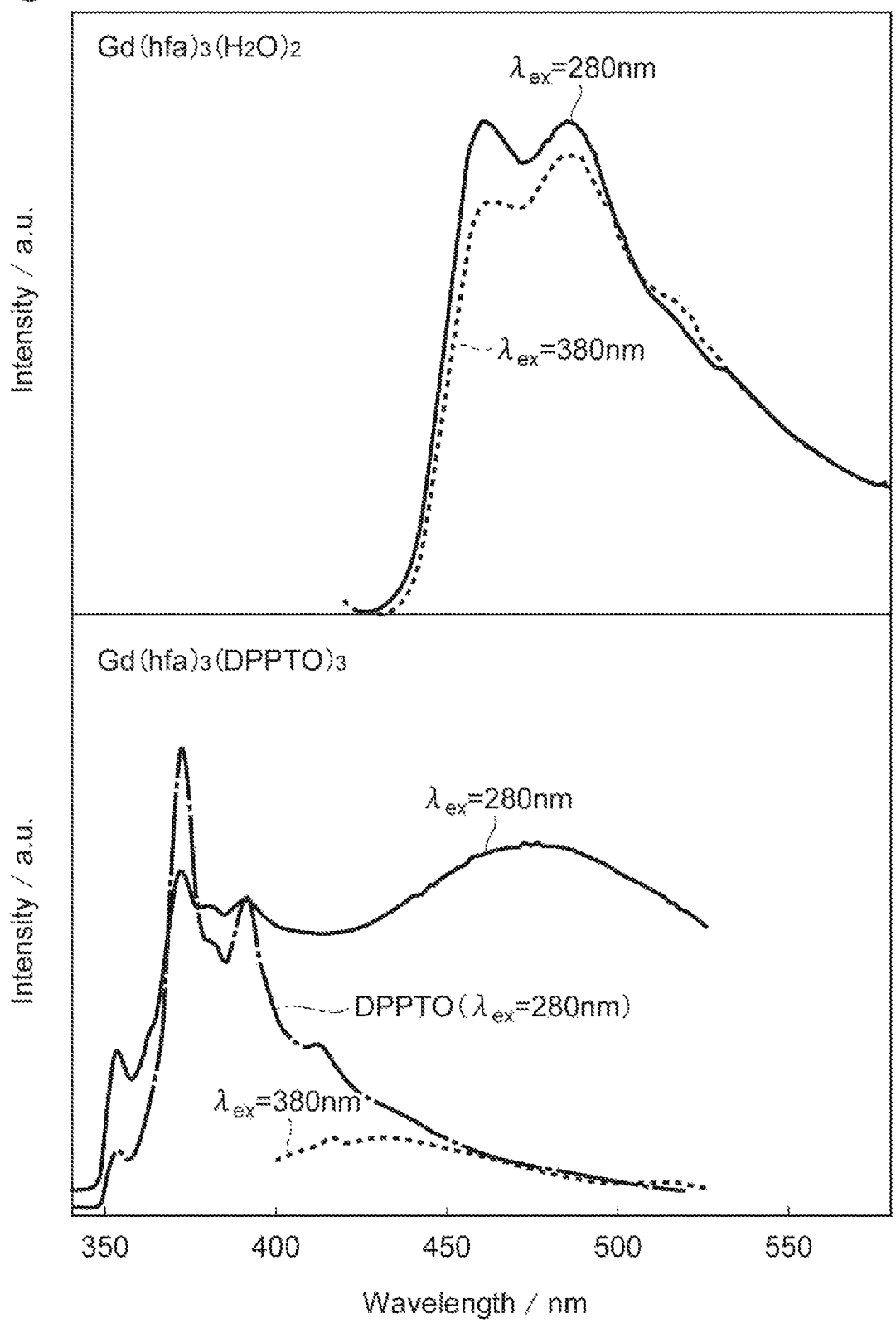
FIG. 1 is an emission spectra of powder of $Gd(hfa)_3(H_2O)_2$ and $Gd(hfa)_3(DPPTO)_3$.

Embodiments of the present invention are described in detail in the following. The present invention, however, is not limited to the following embodiments.

The rare earth complex in an embodiment comprises a rare earth ion and a plurality of ligands coordinated with the rare earth ion.

The rare earth ion is an ion of rare earth element selected from the group consisting of, for example, europium (Eu), neodymium (Nd), ytterbium (Yb), and gadolinium (Gd). For example, europium as a trivalent cation ($Eu^{3+}$) forms a complex.

The rare earth complex in an embodiment has a ligand having a condensed polycyclic aromatic group derived from a condensed polycyclic aromatic compound represented by the following formula (I) or (II). The condensed polycyclic aromatic group is a residue formed by removing a hydrogen atom bonded to a condensed aromatic ring in formula (I) or formula (II) from a condensed polycyclic aromatic compound represented by the following formula (I) or (II). The condensed polycyclic aromatic compound of formula (I) or (II) and a condensed polycyclic aromatic group derived therefrom may have or may not have a substituent (for example, a methyl group) bonded to the condensed ring in formula (I) or formula (II). The condensed polycyclic aromatic group has a π conjugated system having a large area and a large width, which contributes to efficient emission by excitation using visible light in the vicinity of 460 nm. This is supported by calculation of the absorption properties through a semiempirical molecular orbital method as described below.

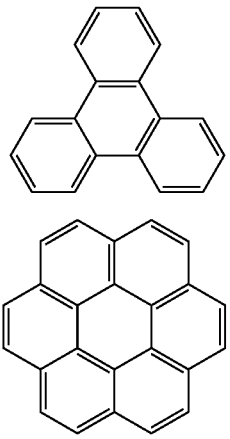

(I)

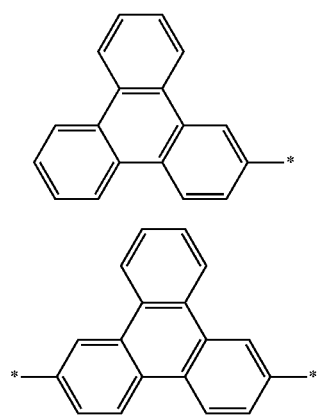

(II)

Specific examples of the condensed polycyclic aromatic group as a residue formed by removing a hydrogen atom from the condensed polycyclic aromatic compound of formula (I) include a monovalent condensed polycyclic aromatic group represented by the following formula (Ia) and a divalent condensed polycyclic aromatic group represented by the following formula (Ib). In these formulas, * represents a bond, which is the same in other formulas.

(Ia)

(Ib)

Specific examples of the condensed polycyclic aromatic group as a residue formed by removing a hydrogen atom from the condensed polycyclic aromatic compound of formula (II) include a monovalent condensed polycyclic aromatic group represented by the following formula (IIa) and a divalent condensed polycyclic aromatic group represented by the following formula (IIb).

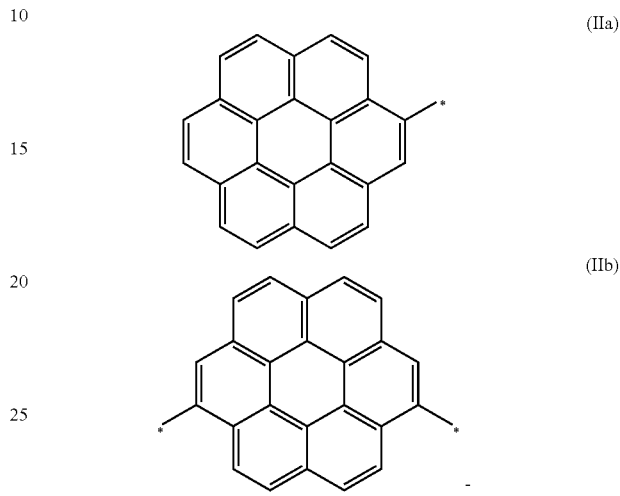

(IIa)

(IIb)

The ligand having a condensed polycyclic aromatic group may be, for example, at least either one of a phosphine oxide ligand represented by the following formula (10) and a diketone ligand represented by the following formula (20).

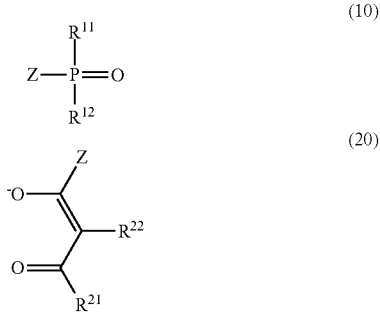

(10)

(20)

In formula (10), Z represents a condensed polycyclic aromatic group derived from a condensed polycyclic aromatic compound of the formula (I) or (II) described above, and $R^{11}$ and $R^{12}$ each independently represent an aryl group different from the condensed polycyclic aromatic group. In formula (20), Z represents a condensed polycyclic aromatic group derived from a condensed polycyclic aromatic compound of the formula (I) or (II) described above, and $R^{21}$ and $R^{22}$ each independently represent a hydrogen atom, an alkyl group, a halogenated alkyl group, an aryl group different from the condensed polycyclic aromatic group, or a heteroaryl group.

The aryl group as $R^{11}$ or $R^{12}$ may be a residue formed by removing a hydrogen atom from an aromatic compound. The aryl group may have, for example, 6 to 14 carbon atoms. Specific examples of the aryl group include a residue formed by removing a hydrogen atom from a substituted or unsubstituted benzene, a substituted or unsubstituted naphthalene, a substituted or unsubstituted anthracene, and a residue formed by removing a hydrogen atom from a substituted or unsubstituted phenanthrene. In particular, $R^{11}$ and $R^{12}$ may be a substituted or unsubstituted phenyl group.

The alkyl group and the halogenated alkyl group as $R^{21}$ or $R^{22}$ may have 1 to 15, 1 to 5, or 1 to 3 carbon atoms. The halogenated alkyl group may be a fluorinated alkyl group such as trifluoromethyl group. Examples of the aryl group and the heteroaryl group as $R^{21}$ or $R^{22}$ include a phenyl group, a naphthyl group, and a thienyl group. $R^{21}$ may be a methyl group, a trifluoromethyl group, a tert-butyl group, or a phenyl group. $R^{22}$ may be a hydrogen atom (including a deuterium atom).

The ligand having a condensed polycyclic aromatic group may be, for example, a bidentate phosphine oxide ligand represented by the following formula (30). Z, $R^{11}$ and $R^{12}$ in formula (30), are similarly defined as Z, $R^{11}$ and $R^{12}$ in formula (10). The phosphine oxide ligand of formula (30) may be coordinated with two rare earth ions such that the rare earth ions are linked.

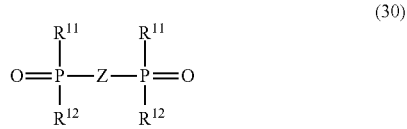
(30)

The rare earth complex may further comprise other ligands in addition to the ligand having a condensed polycyclic aromatic group. Examples of the other ligands include a phosphine oxide ligand represented by the following formula (11) and a diketone ligand represented by the following formula (21).

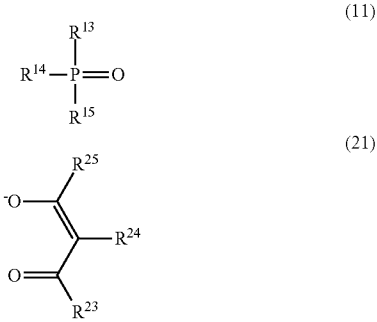

In formula (11), $R^{13}$, $R^{14}$ and $R^{15}$ each independently represent an aryl group different from a condensed polycyclic aromatic group derived from the condensed polycyclic aromatic compound of the formula (I) or (II) described above. Examples of the aryl group as $R^{13}$, $R^{14}$ or $R^{15}$ include those which are the same as $R^{11}$ or $R^{12}$ in formula (10). $R^{13}$, $R^{14}$ and $R^{15}$ may be a substituted or unsubstituted phenyl group.

In formula (21), $R^{23}$, $R^{24}$ and $R^{25}$ each independently represent a hydrogen atom, an alkyl group, a halogenated alkyl group, an aryl group different from a condensed polycyclic aromatic group derived from the condensed polycyclic aromatic compound of the formula (I) or (II) described above, or a heteroaryl group. Examples of $R^{23}$, $R^{24}$ and $R^{25}$ include those which are the same as $R^{21}$ and $R^{22}$ in formula (20). $R^{23}$ and $R^{25}$ may be each independently a methyl group, a trifluoromethyl group, a tert-butyl group or a phenyl group, and $R^{24}$ may be a hydrogen atom (including a deuterium atom).

The rare earth complex containing a diketone ligand represented by formula (20) or (21) is able to have further excellent properties from the viewpoints of intensive emission and the like. As a ligand of the rare earth complex, a combination of a diketone ligand represented by formula (20) having a condensed polycyclic aromatic group and a phosphine oxide ligand represented by formula (11), or a combination of a diketone ligand represented by formula (21) and a ligand represented by formula (10) having a condensed polycyclic aromatic group, may be therefore selected. For example, the rare earth complex may be a complex represented by the following formula (C1) or (C2). In formulas (C1) and (C2), Ln (III) represents a trivalent rare earth ion.

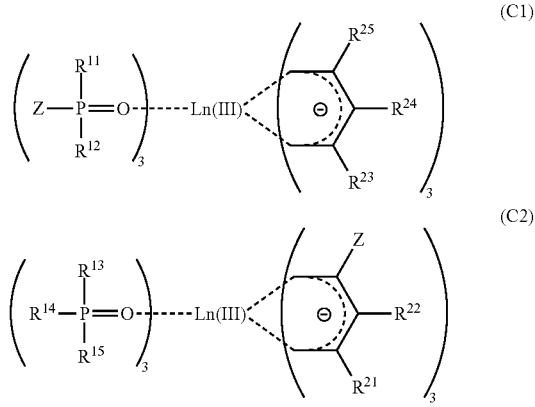

The rare earth complex having a diketone ligand may have a bidentate ligand represented by formula (30). Examples thereof include a complex represented by the following (C3). The definition of each symbol in formula (C3) is the same as described above. In the complex represented by formula (C3), two rare earth ions Ln (III) are linked through two bidentate ligands.

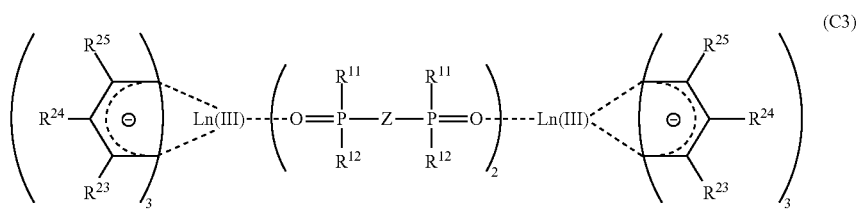
(C3)

The light emitting element comprising the rare earth complex of the present embodiment is expected to be applied to, for example, the light source of a white LED element excited by a blue LED and an optical coherence tomography (OCT) apparatus. A rare earth complex in several embodiments allows a light emitting element with a wide band width of 140 nm or more, or 200 nm or more, to be provided at a low cost. The band width, for example, directly affects the resolution of OCT, and high resolution can be obtained by using a light source having a wide band width.

EXAMPLES

The present invention will be described in further detail based on Examples as follows. However, the present invention is not limited to the following Examples.

1. Synthesis of Rare Earth Complex (1) Synthesis of $Gd(hfa)_3(DPPTO)_3$

In toluene (15 mL), tris(hexafluoroacetylacetonate)gadolinium ($Gd(hfa)_3(H_2O)_2$, 350 mg, 0.430 mmol) and 2-diphenylphosphoryltriphenylene DPPTO (500 mg, 1.17 mmol) were dissolved, and the resulting reaction solution was heated to reflux at 85° C. for 12 hours. Subsequently, the reaction solution was dried and solidified by an evaporator. Using a mixed solvent of dichloromethane/hexane, the residue was re-precipitated, and the precipitate was washed with hexane to obtain $Gd(hfa)_3(DPPTO)_3$ (white powder), (yield: 78 mg, yield rate: 13%).

Elemental analysis (%): calcd for $C_{105}H_{66}GdF_{18}O_9P_3$: C 61.11, H 3.22. Found: C 62.53, H 3.53.

ESI-MS: m/z calcd for $C_{100}H_{65}GdF_{12}O_7P_3$ [M-hfa]$^+$=1856.30; found: 1856.35.

(2) Synthesis of $Eu(hfa)_3(DPPTO)_3$

In toluene (10 mL), tris(hexafluoroacetylacetonate) europium ($Eu(hfa)_3(H_2O)_2$, 350 mg, 0.430 mmol) and 2-diphenylphosphoryltriphenylene (DPPTO, 300 mg, 0.701 mmol) were dissolved, and the resulting reaction solution was heated to reflux at 85° C. for 12 hours. Subsequently, the reaction solution was dried and solidified by an evaporator. Using a mixed solvent of dichloromethane/hexane, the residue was re-precipitated, and the precipitate washed with hexane to obtain $Eu(hfa)_3(DPPTO)_3$ (white powder), (yield: 82 mg, yield rate: 17%).

Elemental analysis (%): calcd for $C_{105}H_{66}EuF_{18}O_9P_3$: C 61.26, H 3.23. Found: C 61.40, H 3.41

ESI-MS: m/z calcd for $C_{100}H_{65}EuF_{12}O_7P_3$ [M-hfa]$^+$=1851.30; found: 1851.32.

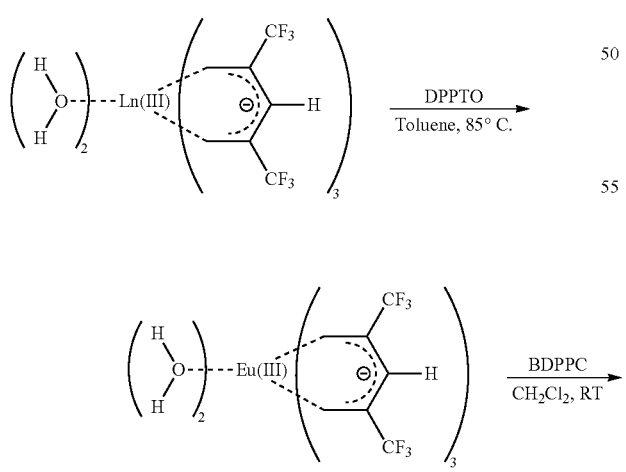

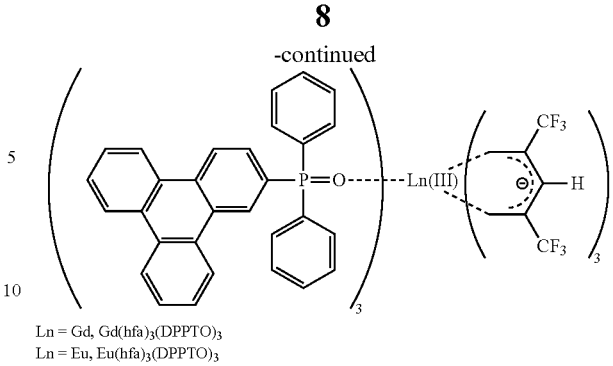

Ln = Gd, $Gd(hfa)_3(DPPTO)_3$
Ln = Eu, $Eu(hfa)_3(DPPTO)_3$ (3) Synthesis of $Eu_2(hfa)_6(BDPPC)_2$ Synthesis of 1,6-bis(diphenylphosphoryl)coronene (BDPPC):

In chlorobenzene (300 mL), coronene (6.3 g, 20.9 mmol) was suspended, and a mixture of chlorobenzene (100 mL) and bromine (10.0 g, 62.6 mmol) was added dropwise thereto. The formed reaction liquid was heated at 70° C. for 15 minutes while stirring, and then cooled with ice for 20 minutes. After completion of stirring, the reaction liquid was left standing and subjected to decantation. A solid taken out by suction filtration was washed with chlorobenzene and hexane and then dried, so that a yellow solid containing dibromocoronene (7.4 g) was obtained.

The resulting yellow solid was suspended in ultra-dehydrated THF (250 mL). Thereto, n-butyllithium (8.5 mL, 14 mmol) was added and the suspension was stirred. After 2 hours, chlorodiphenylphosphine (2.4 mL, 13 mmol) was added thereto, so that the suspension turned into a transparent solution. To the solution, $H_2O_2$ (2 mL) was added and stirred for 3 hours. Subsequently, extraction from the solution was performed three times with dichloromethane and brine. The dichloromethane layer was dried and solidified, and the resulting crude product solid was purified by silica column chromatography (dichloromethane/ethyl acetate), so that BDPPC was obtained.

$^1$H-NMR (CDCl$_3$, 400 MHz): /ppm=10.03-8.60 (m, 10H), 7.99-7.40 (m, 20H)

Synthesis of $Eu_2(hfa)_6(BDPPC)_2$

In dichloromethane (20 mL), tris(hexafluoroacetylacetonate)europium ($Eu(hfa)_3(H_2O)_2$, 65 mg, 0.08 mmol) and BDPPC (50 mg, 0.07 mmol) were dissolved, and the resulting reaction solution was stirred at room temperature for 4 hours. Subsequently, the reaction solution was dried and solidified by an evaporator. The solidified crude product was purified by recrystallization using a mixed solvent of dichloromethane/hexane, so that $Eu_2(hfa)_6(BDPPC)_2$ (yellow powder) was obtained (yield: 10 mg, yield rate: 5%).

ESI-MS: m/z calcd for $C_{121}H_{65}Eu_2F_{30}O_{14}P_4$ [M-hfa]+=2740.13; found: 2740.08.

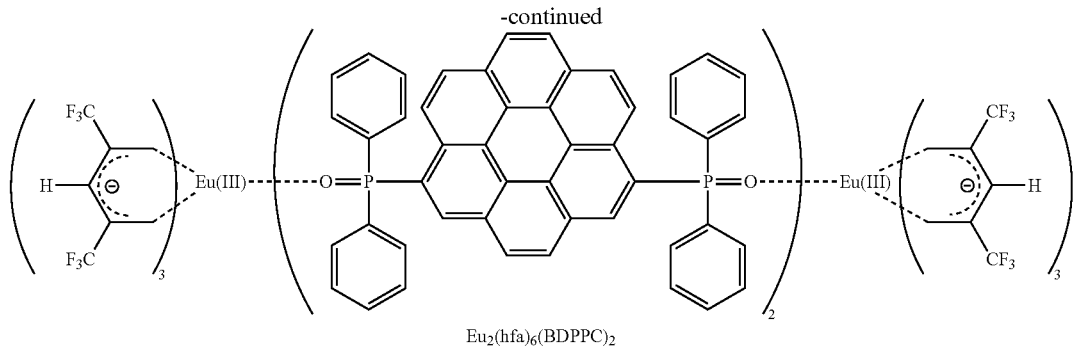

Eu₂(hfa)₆(BDPPC)₂

2. Photophysical Properties of Gd(hfa)₃(DPPTO)₃

FIG. 1 is a graph showing emission spectra of powder of Gd(hfa)₃(H₂O)₂ and Gd(hfa)₃(DPPTO)₃. Excitation wavelength λex was set to 280 nm or 380 nm. In the emission spectrum of Gd(hfa)₃(H₂O)₂, phosphorescence derived from hfa was observed in the vicinity of 470 nm. In the emission spectrum of Gd(hfa)₃(DPPTO)₃, emission bands were observed in the vicinity of 370 nm and in the vicinity of 470 nm when excitation light was at 280 nm. Since the emission band on the short-wavelength side coincides with the fluorescence of a single DPPTO in ligand, it is believed that the emission band is derived from the fluorescence of the DPPTO ligand in the complex. Since the emission band on the long-wavelength side allows the wavelength region to overlap with the phosphorescent band of hfa in Gd(hfa)₃(H₂O)₂, it is believed that phosphorescence of the hfa ligand was mainly observed. On the other hand, when the excitation light was at 380 nm, an emission band of Gd(hfa)₃(DPPTO)₃ was observed in the vicinity of 430 nm. Since the energy of the emission band is close to the energy of a single DPPTO ligand (in a solution or powder condition) in a $T_1$ state, it is believed that the emission band in the vicinity of 430 nm was mainly assigned to the phosphorescence of the DPPTO ligand in Gd(hfa)₃(DPPTO)₃. These results suggest that when Gd(hfa)₃(DPPTO)₃ is excited by light having a wavelength of 380 nm, a DPPTO ligand in an excited triplet state is mainly formed.

3. Photophysical Properties of Eu(hfa)₃(DPPTO)₃

<Excited Emission Spectrum>

Figure 2:
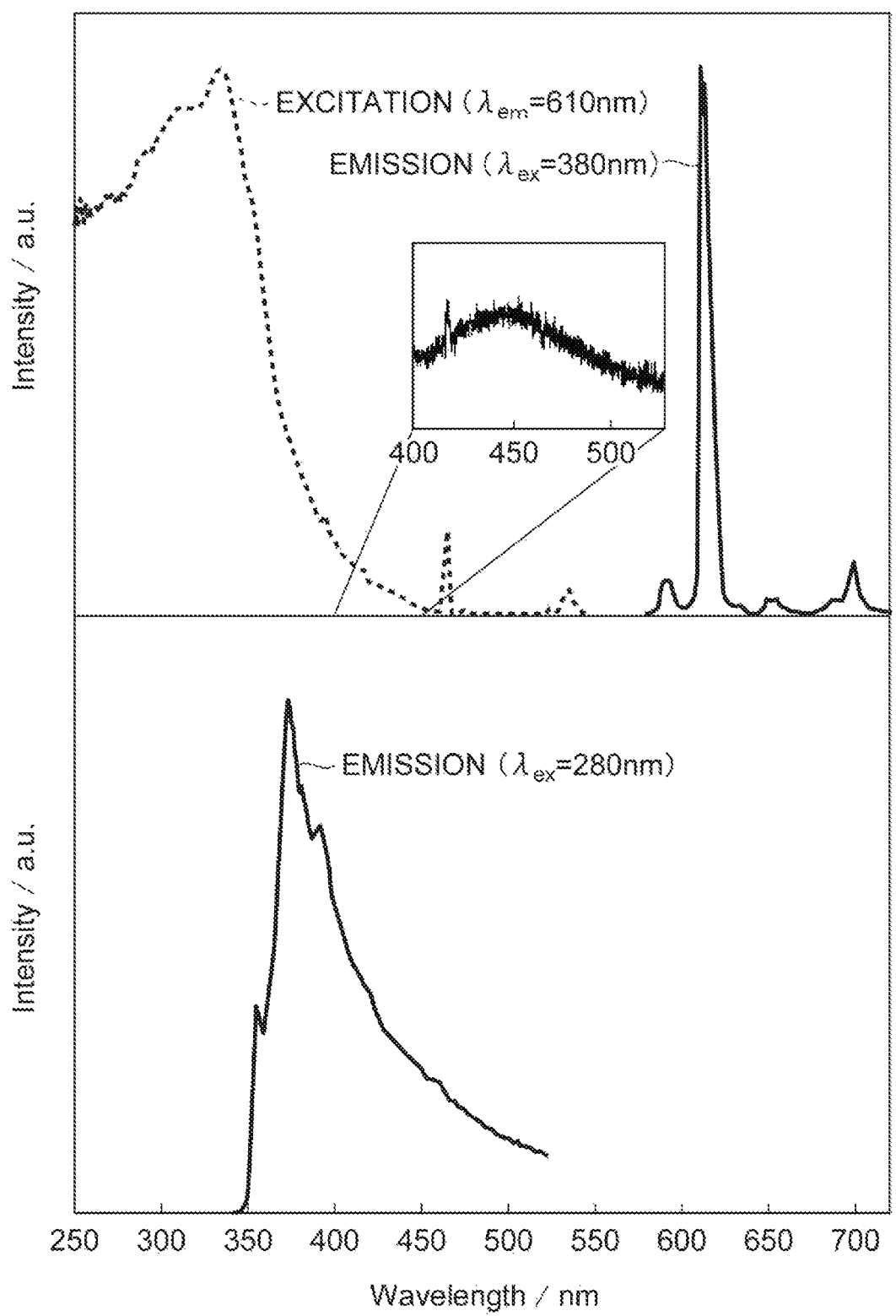
FIG. 2 is an excitation and emission spectra of powder of $Eu(hfa)_3(DPPTO)_3$.

FIG. 2 is a graph showing excitation and emission spectra of powder of Eu(hfa)₃(DPPTO)₃. The spectra shown on the upper side in FIG. 2 are an excitation spectrum having a fluorescence wavelength λem of 610 nm and an emission spectrum having an excitation wavelength λex of 380 nm. The spectrum shown on the lower side in FIG. 2 is an emission spectrum having an excitation wavelength λex of 280 nm. When the excitation wavelength was 380 nm, emission bands were observed at 579 nm, 593 nm, 613 nm, 650 nm and 700 nm, corresponding to $^5D_0 \rightarrow ^7F_0$, $^5D_0 \rightarrow ^7F_1$, $^5D_0 \rightarrow ^7F_2$, $^5D_0 \rightarrow ^7F_3$, and $^5D_0 \rightarrow ^7F_4$, respectively.

In the emission spectrum having excitation wavelength of 380 nm, a broad emission band was observed in the vicinity of 445 nm. The wavelength is shifted to the longer-wavelength side than the phosphorescence wavelength of DPPTO (439 nm) estimated from the emission spectrum of Gd(hfa)₃(DPPTO)₃. This suggests that an LMCT excited state based on the transition from DPPTO ligand to Eu (III) is mixed with the $T_1$ state.

In the emission spectrum having an excitation wavelength of 280 nm, the fluorescence of DPPTO was observed in the vicinity of 370 nm in the same manner as in the case of Gd(hfa)₃(DPPTO)₃. This suggests that the DPPTO ligand is not substantially subjected to the internal heavy atom effect of Eu (III).

<Emission Life>

The emission life of Eu(hfa)₃(DPPTO)₃ in a powder condition was measured. In Table 1, together with the observed emission life $\tau_{obs}$, the emission quantum yield $\phi_{ff}$ of 4f-4f transition determined from the emission life measurement, the emission quantum efficiency $\phi_{\pi\pi^*}$ of π-π* transition, the radiative constant $\kappa_r$, the nonradiative constant $\kappa_{nr}$, and the energy transfer efficiency $\eta_{sens}$ are shown. In Table 1, literature data on Eu(hfa)₃(TPPO)₂ are also shown (A. Nakajima, T. Nakanishi, Y. Kitagawa, T. Seki, H. Ito, K. Fushimi, Y. Hasegawa, Sci. Rep. 6, 24458 (2016)).

TABLE 1

| | $\tau_{obs}$/ ms | $k_r/s^{-1}$ | $k_{nr}/s^{-1}$ | $\Phi_{ff}$/ % | $\Phi_{\pi\pi^*}$/ % | $\eta_{sens}$/ % |
|---|---|---|---|---|---|---|
| Eu(hfa)₃(DPPTO)₃ | 0.77 | 9.1 × 10² | 3.8 × 10² | 70 | 32 | 45 |
| Eu(hfa)₃(TPPO)₂ | 0.80 | 8.1 × 10² | 4.4 × 10² | 65 | 51 | 78 |

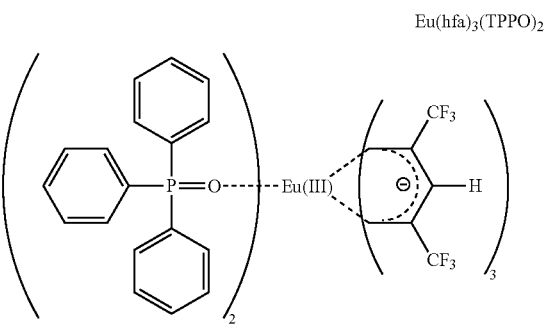

Eu(hfa)₃(TPPO)₂

Eu(hfa)₃(DPPTO)₃ exhibited a higher emission quantum yield $\phi_{ff}$ than Eu(hfa)₃(TPPO)₂.

4. Evaluation on Absorption Intensity by Simulation

Figure 3:
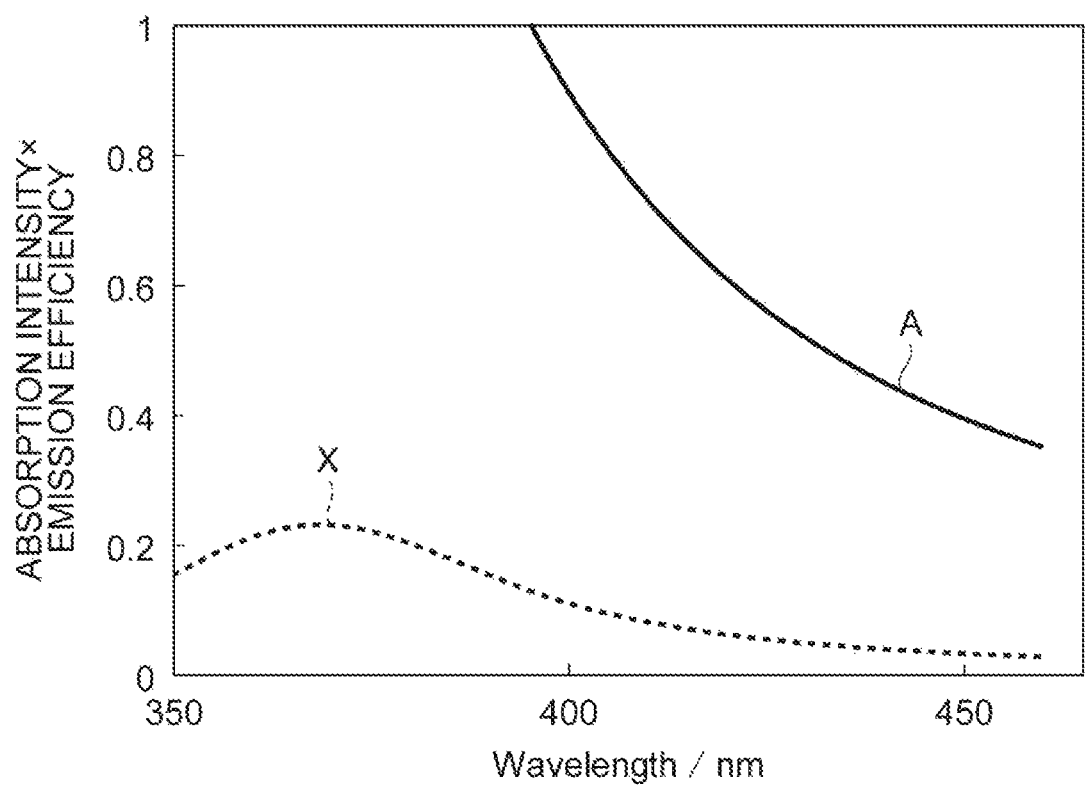
FIG. 3 is a graph showing calculation results of relations between absorption intensity×emission efficiency and wavelength on $Eu(hfa)_3(DPPTO)_3$ and $Eu(hfa)_3(HPO)_2$.

The optical absorption properties of Eu(hfa)₃(DPPTO)₃ were compared with those of Eu(hfa)₃(HPO)₂ by simulation. The simulation was performed by a semiempirical molecular orbital method using a quantum chemistry calculation software Gaussian. FIG. 3 is a graph showing calculation results of relations between absorption intensity×emission efficiency and wavelength on Eu(hfa)₃(DPPTO)₃ and Eu(hfa)₃

(HPO)$_2$. In the graph, A represents Eu(hfa)$_3$(DPPTO)$_3$ and X represents Eu(hfa)$_3$(HPO)$_2$. It is suggested that Eu(hfa)$_3$(DPPTO)$_3$ exhibits emission intensity about 15 times that of Eu(hfa)$_3$(HPO)$_2$ in the vicinity of 460 nm.

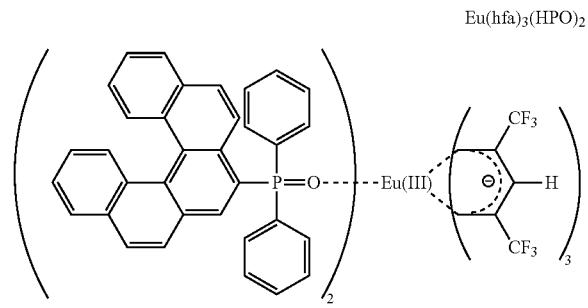

Eu(hfa)$_3$(HPO)$_2$

Figure 4:
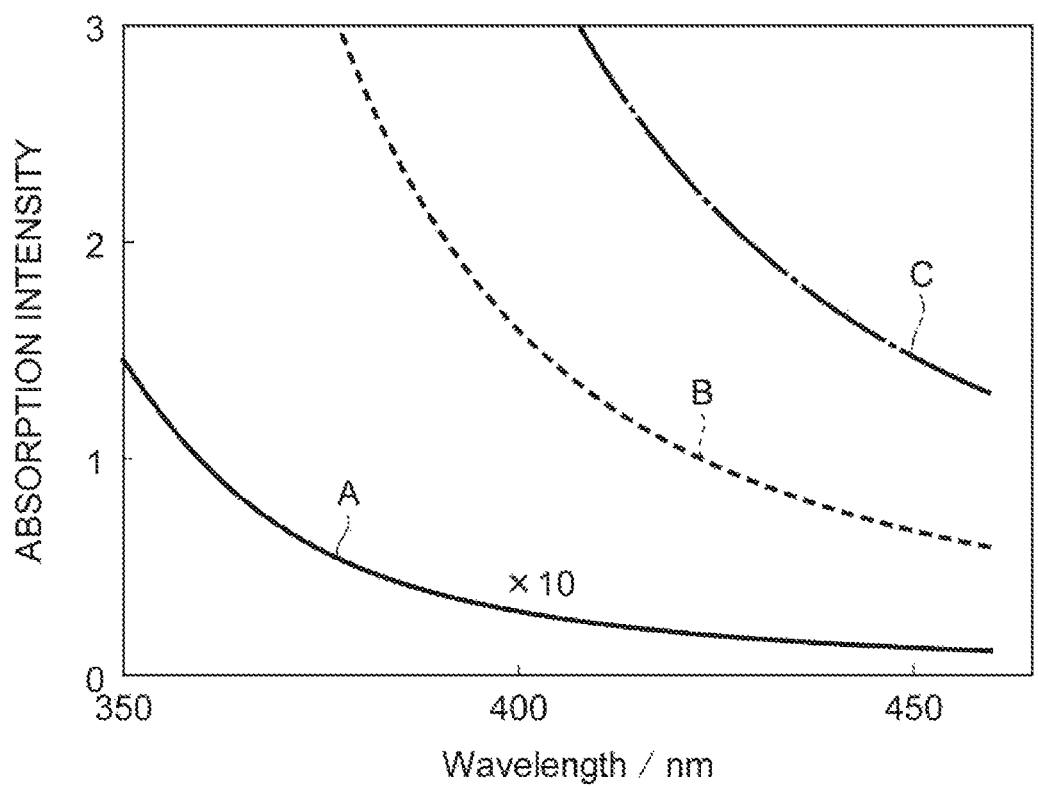
FIG. 4 is a graph showing calculation results of relations between absorption intensity and wavelength on $Eu(hfa)_3(DPPTO)_3$ and designed rare earth complexes.

Furthermore, the following rare earth complexes having a diketone ligand with a condensed polycyclic aromatic group (Complex B and Complex C) were designed, of which optical absorption properties were also calculated by simulation. FIG. 4 is a graph showing calculation results of relations between absorption intensity and wavelength on Eu(hfa)$_3$(DPPTO)$_3$, Complex B and Complex C. In the graph, A represents Eu(hfa)$_3$(DPPTO)$_3$, B represents Complex B, and C represents Complex C. It was suggested that Complex B and Complex C exhibit larger emission intensity greatly increased in the vicinity of 460 nm than Eu(hfa)$_3$(DPPTO)$_3$.

Complex B

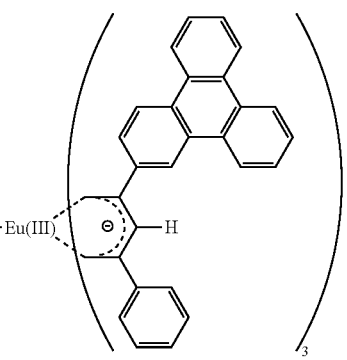

Complex C

5. Photophysical Properties of Eu$_2$(hfa)$_6$(BDPPC)$_2$

Figure 5:
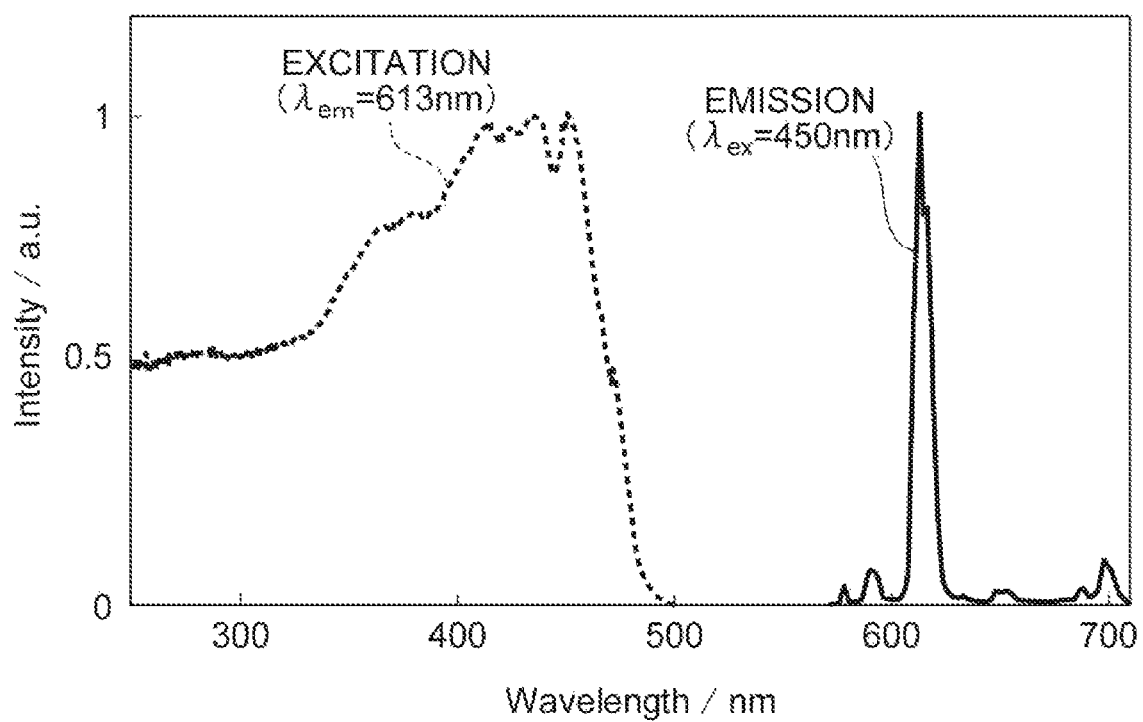
FIG. 5 is an excitation and emission spectra of powder of $Eu_2(hfa)_6(BDPPC)_2$.

FIG. 5 is a graph showing excitation and emission spectra of powder of Eu$_2$(hfa)$_6$(BDPPC)$_2$. In FIG. 5, an excitation spectrum having a fluorescence wavelength λem of 613 nm and an emission spectrum having an excitation wavelength λex of 450 nm are shown. It was confirmed that the powder of Eu$_2$(hfa)$_6$(BDPPC)$_2$ exhibits the highest emission intensity with excitation light of 460 nm and emits light even with long-wavelength excitation light of about 500 nm.

Figure 6:
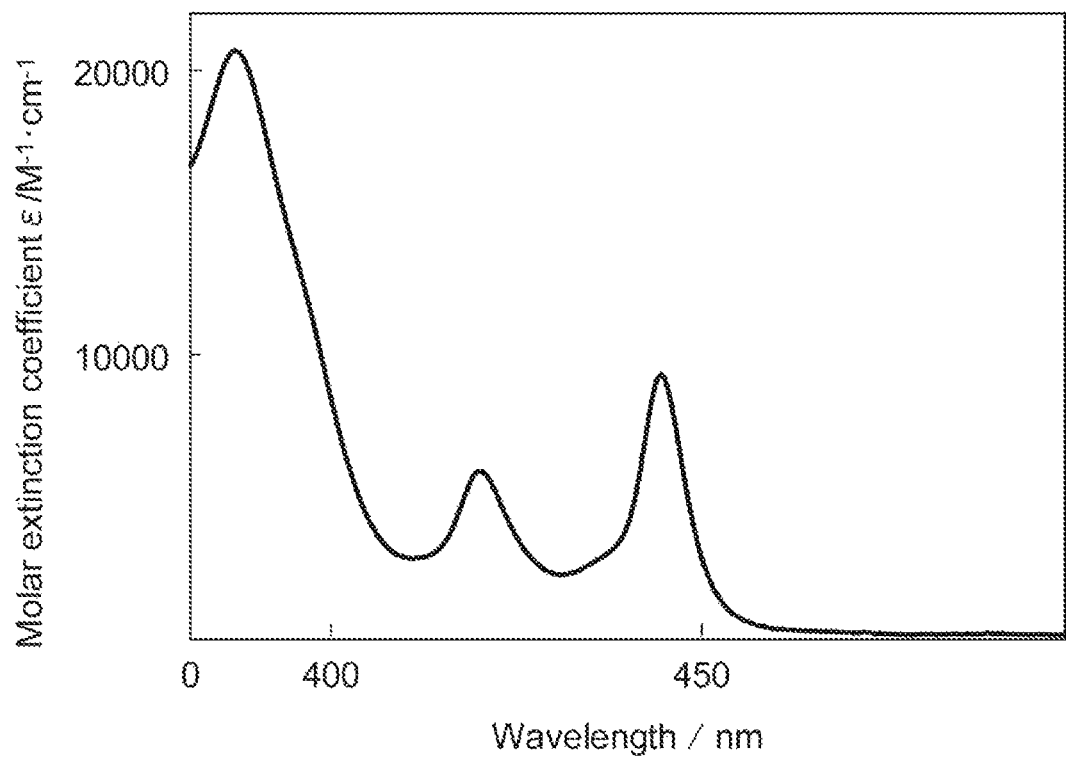
FIG. 6 is an absorption spectrum of a chloroform solution containing $Eu_2(hfa)_6(BDPPC)_2$ at a low concentration.

The molar extinction coefficient c of Eu$_2$(hfa)$_6$(BDPPC)$_2$ in chloroform and the emission efficiency (room temperature) of Eu (III) when organic ligands are excited were measured. FIG. 6 is a graph showing an absorption spectrum of a chloroform solution containing Eu$_2$(hfa)$_6$(BDPPC)$_2$ at a low concentration. A deuterated chloroform solution of Eu(hfa)$_3$(TPPO)$_2$ and a chloroform solution of Eu(hfa)$_3$(HPO)$_2$ were prepared, and the molar extinction coefficient and the emission efficiency thereof were also measured.

TABLE 2

|  |  | Eu(hfa)$_3$(TPPO)$_2$ (CDCl$_3$ solution) | Eu(hfa)$_3$(HPO)$_2$ (CHCl$_3$ solution) | Eu$_2$(hfa)$_6$(BDPPC)$_2$ (CHCl$_3$ solution) |
|---|---|---|---|---|
| Molar extinction coefficient/ M$^{-1}$ · cm$^{-1}$ | 390 nm | 9 | 3000 | 19000 |
|  | 450 nm | 0.7 | 100 | 3000 |
| Emission efficiency |  | 59% | 4%[a] | 34% |

[a] The emission efficiency of Eu(hfa)$_3$(HPO)$_2$ was measured at powder.

From the results shown in Table 2, it was suggested that Eu$_2$(hfa)$_6$(BDPPC)$_2$ emits light with an intensity about 2000 times that of Eu(hfa)$_3$(TPPO)$_2$ and with an intensity about 200 times that of Eu(hfa)$_3$(HPO)$_2$, by excitation light of 450 nm. In the case of excitation light of 460 nm also, it is believed that Eu$_2$(hfa)$_6$(BDPPC)$_2$ exhibits high emission intensity in the same manner. When the chloroform solution of Eu$_2$(hfa)$_6$(BDPPC)$_2$ was irradiated with blue light of 458 nm, high-intensity emission of red light of Eu(III) was observed.

INDUSTRIAL APPLICABILITY

The rare earth complex of the present invention and a light emitting element comprising the same are usable as a blue LED-type white LED and a light source for OCT. Further, expected applications include a solvent sensor which uses changes in emission properties depending on types of solvent, a temperature sensor which uses variation in properties with temperature, and a circularly polarized light-emitting substance.

The invention claimed is:

1. A rare earth complex comprising:
a rare earth ion; and
a ligand coordinated with the rare earth ion and having a condensed polycyclic aromatic group,
wherein the condensed polycyclic aromatic group is a residue formed by removing a hydrogen atom bonded to a condensed aromatic ring in the following formula (I) or formula (II) from a condensed polycyclic aromatic compound represented by formula (I) or (II), and
the condensed polycyclic aromatic compound optionally has a substituent bonded to the condensed aromatic ring in formula (I) or formula (II),

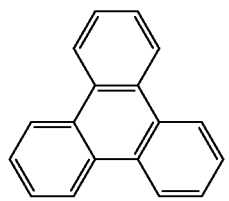

(I)

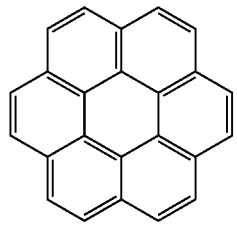

(II)

wherein the ligand having the condensed polycyclic aromatic group is a phosphine oxide ligand having one phosphine oxide group and represented by the following formula (10):

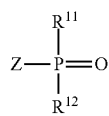

(10)

wherein in formula (10), Z represents the condensed polycyclic aromatic group and R$^{11}$ and R$^{12}$ each independently represent an aryl group different from the condensed polycyclic aromatic group, and the rare earth complex further comprises a diketone ligand represented by the following formula (21) and coordinated with the rare earth ion:

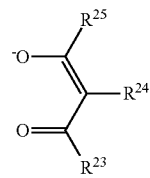

(21)

wherein R$^{23}$, R$^{24}$ and R$^{25}$ each independently represent a hydrogen atom, an alkyl group, a halogenated alkyl group, an aryl group different from the condensed polycyclic aromatic group, or a heteroaryl group.

2. A light emitting element comprising the rare earth complex according to claim 1.

3. A rare earth complex comprising:
two rare earth ions; and
a ligand coordinated with each of the rare earth ions and having a condensed polycyclic aromatic group,
wherein the condensed polycyclic aromatic group is a residue formed by removing two hydrogen atoms bonded to the condensed aromatic ring in the following formula (I) or formula (II) from a condensed polycyclic aromatic compound represented by formula (I) or (II), and
the condensed polycyclic aromatic compound optionally has a substituent bonded to the condensed aromatic ring in formula (I) or formula (II),

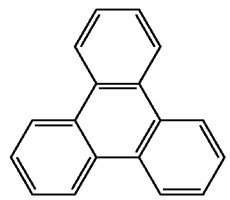

(I)

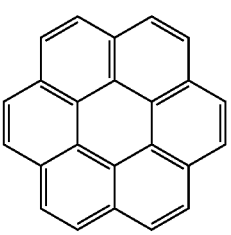

(II)

wherein the ligand having the condensed polycyclic aromatic group is a bidentate phosphine oxide ligand represented by the following formula (30), and the phosphine oxide ligand is coordinated with two of the rare earth ions:

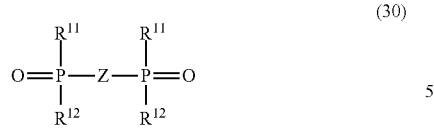

(30)

wherein Z represents the condensed polycyclic aromatic group, and $R^{11}$ and $R^{12}$ each independently represent an aryl group different from the condensed polycyclic aromatic group.

4. The rare earth complex according to claim 3, further comprising a diketone-ligand represented by the following formula (21) and coordinated with one of the two rare earth ions:

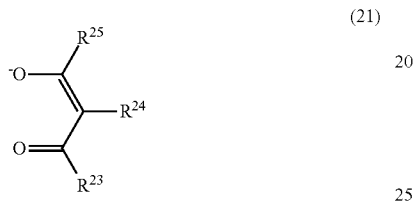

(21)

wherein $R^{23}$, $R^{24}$ and $R^{25}$ each independently represent a hydrogen atom, an alkyl group, a halogenated alkyl group, an aryl group different from the condensed polycyclic aromatic group, or a heteroaryl group.

5. A light emitting element comprising the rare earth complex according to claim 3.

* * * * *